United States Patent [19]

Yelderman

[11] Patent Number: 4,507,974
[45] Date of Patent: Apr. 2, 1985

[54] METHOD AND APPARATUS FOR MEASURING FLOW

[75] Inventor: Mark L. Yelderman, Menlo Park, Calif.

[73] Assignee: The Board of Trustees of the Leland Stanford Jr. University, Stanford, Calif.

[21] Appl. No.: 487,334

[22] Filed: Apr. 21, 1983

[51] Int. Cl.³ .......................... G01F 1/70; G01F 1/68
[52] U.S. Cl. ................................ 73/861.06; 128/713; 364/510
[58] Field of Search .................... 73/861.06, 861.31; 364/824, 728, 604, 510, 819; 128/713

[56] References Cited

U.S. PATENT DOCUMENTS

| | | | |
|---|---|---|---|
| 3,214,973 | 11/1965 | Lester | 73/861.31 |
| 3,842,670 | 10/1974 | Brain | 73/861.05 |
| 4,035,622 | 7/1977 | Obermajer | 128/713 |
| 4,244,026 | 1/1981 | Dickey, Jr. | 364/728 X |

OTHER PUBLICATIONS

UK Patent Application, M. Heard, Measuring flow or movement, 9/4/1980, Application No. 8028649.

Primary Examiner—Charles A. Ruehl
Assistant Examiner—Brian R. Tumm
Attorney, Agent, or Firm—Townsend and Townsend

[57] ABSTRACT

Flow, and in particular nonuniform flow, as in a vascular system, is measured by applying a stochastic excitation signal to a system inlet which results in a measurable output signal at a downstream system outlet. Flow rate may be extracted by cross-correlating the excitation signal and the output signal. Calibration may be effected by conservation of mass principles whereby quantity type parameters are related to concentration type parameters. The stochastic signal has the characteristics of white noise, such that simplified spread spectral detection and signal extraction techniques may be employed to recover the desired intelligence.

20 Claims, 1 Drawing Figure

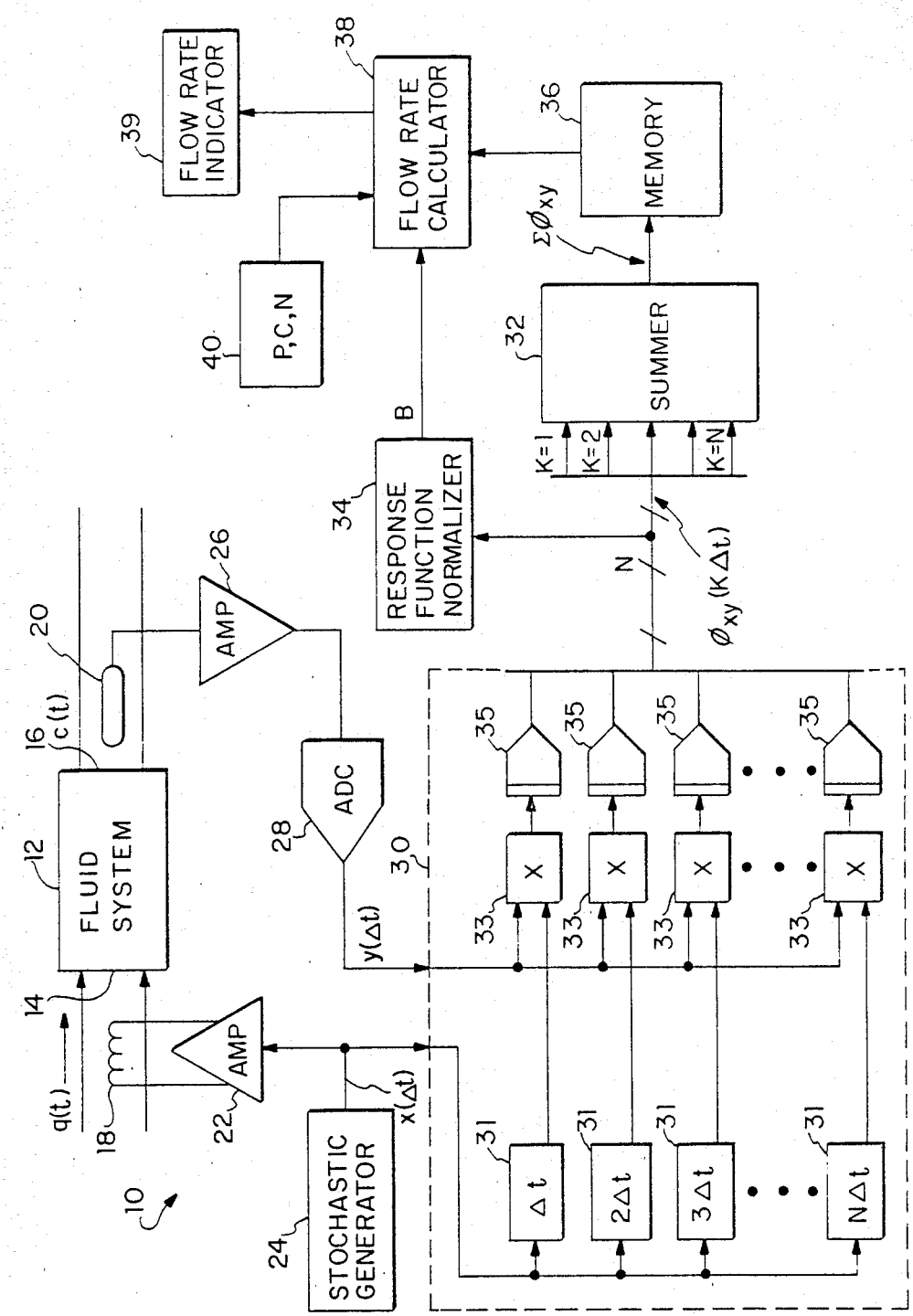
FIG._1

METHOD AND APPARATUS FOR MEASURING FLOW

This invention was made with Government support under Contract No. RO1 HL24798 awarded by the National Institutes of Health. The Government has certain rights in this invention.

BACKGROUND OF THE INVENTION

1. Field of Invention

This invention relates to flow measurement and particularly to in vivo blood flow measurement. As used herein flow is the measurement of fluid movement expressed in terms of a product of fluid density and fluid velocity. Blood flow measurement is an important diagnostic technique used in various medical applications. A prime application is in the diagnostic analysis and treatment of heart conditions, where accurate flow rate measurement can be extremely useful.

2. Description of the Prior Art

Various techniques have been developed for measuring flow, and specifically measuring the volume flux or average flow rate of blood as an incompressible fluid in a vascular system. One such technique is an indicator dilution technique wherein a sterile marking dye is injected, either as an impulse or continuously, in exact measurement into a cardiovascular system and then the concentration is sensed at a downstream measuring point. A flow rate can be computed based on conservation of mass principles. Such a technique however requires a number of assumptions regarding the system, and the technique can be very time consuming.

A thermodilution technique is known for measuring flow which employs an instrumented catheter inserted through the area where flow is to be measured. A four-lumen catheter developed by Swan & Ganz employs the injection of a quantity of heat, such as a hot or cold saline solution, through the catheter upstream of the measuring point. Change in temperature downstream of the measuring point is measured by a thermometer. Flow is computed by analysis of the change in temperature with time. As with the dye injection technique, the Swan-Ganz technique employs injections of a sterile foreign substance and is inherently intermittent in its operation.

It is known that fluid flow can be calculated in a closed system from a dispersion function. The dispersion function is generally an impulse response function obtained as a result of the administration of an indicator by means of an impulse injection. Other deterministic approaches, such as step response measurement and sinusoidal response measurement have also been employed to calculate fluid flow.

Both of the above prior art techniques rely on conservation of mass principles. All of these techniques are basically deterministic in nature and rely on assumptions which may not necessarily be true. For example, the assumption is made that the flow of the indicator is representative of the flow of the total fluid and that the distribution of transit times between the point of origin and the point of measurement is the same for elements of both the total fluid and of the indicator. Moreover, it is assumed that the indicator control volume is constant between a single inlet port and a single outlet port, and that there is no recirculation from the outlet port to the inlet port during the period of measurement. Furthermore, assumptions are made that the mean transit time can be calculated by the mean arrival time of the volume of indicator at the point of measurement.

Techniques are known in the signal processing art for measuring electronic system impulse response by application of nondeterministic signal excitation. Such techniques are heretofore used generally only in communications applications.

What is needed is a flow measuring technique, and particularly a blood flow measuring technique, which is substantially immune to uncertainties associated with deterministic measuring techniques.

SUMMARY OF THE INVENTION

According to the invention, flow, and in particular nonuniform flow as in a vascular system, is measured by applying a simulated random signal or a pure random signal which is measured, such as a stochastic (purely random) signal as an excitation signal to the system inlet which results in a measurable output signal at a downstream system outlet. Flow rate may be extracted by analysis of the cross-correlation of the excitation signal and the output signal. Calibration may be effected by conservation of mass principles whereby quantity type parameters are related to concentration type parameters. The stochastic excitation signal has the characteristics of white noise such that simplified spread spectral detection and signal extraction techniques may be employed to recover the desired intelligence. In a specific embodiment, an injected signal in the form of an indicator modulates temperature or a like detectable parameter, causing an effect which is propogated with the flow of fluid to a point of detection according to the dispersion function of the system under measurement. The preferred simulated stochastic input signal, in the form of a pseudo-random binary sequence, is cross-correlated with a signal received at a point of detection to obtain an output signal representative of a cross-correlation function from which the flow rate may be calculated. Specifically, the cross-correlation function is integrated as if it were a system dispersion function to obtain a moment value from which flow may be computed.

It is an object of the invention to provide a stochastic approach to the problem of deriving the dispersion function related with flow.

It is further an object of the invention to avoid the introduction of errors inherent in assumptions related to deterministic approaches for obtaining the dispersion function, such as the impulse response approach, the step response approach, or the sinusoidal excitation response approach.

It is a still further object of the invention to provide a technique for measuring in vivo blood flow.

The invention will be better understood by reference to the following detailed description taken in connection with the accompanying drawing.

BRIEF DESCRIPTION OF THE DRAWING

FIG. 1 is a block diagram of an apparatus for measuring flow according to the invention.

DETAILED DESCRIPTION OF SPECIFIC EMBODIMENTS

In order to understand the invention, it is helpful to review the technique by which flow is measured.

By conservation of mass, the volume q entering a system or control volume is equal to the integral with respect to time of the flow rate F times the time-dependent concentration function c(t) or:

$$q = \int_T Fc(t)dt \tag{1}$$

A dispersion function is a function which describes the distribution of transit times between two points of a concentration function c(t) or:

$$h(t) = \frac{Fc(t)}{q} \tag{2}$$

where h(t) is the dispersion function, assuming no recirculation.

The dispersion function in a vascular system is the normalized unit impulse response of a vascular segment between sampling sites. It can be used to describe deformation, dispersion and delay, and it can also be used to compute flow. For example, by well known principles, it can be shown that the flow rate of a fluid is equal to the volume divided by the mean arrival time of all elements of a population or:

$$F = V/\bar{t} = \frac{q}{\Sigma h(t)} \tag{3}$$

where V is the volume and t is the mean arrival time of the indicator.

The mean arrival time represents the first moment or integral of a function describing the population distribution of a volume at an arrival point. In this instance, the dispersion function h(t) is the population distribution. Thus by finding the dispersion function, flow can be calculated in connection with other assumptions.

According to the invention, the dispersion function for flow is found by applying a spread spectral or known simulated or actual stochastic excitation signal at a system entry point, sensing the time-dependent response at a system exit point and cross-correlating the excitation signal with the response signal to construct the dispersion function. Flow can then be calculated with reference to calibration parameters.

It can be shown that the dispersion function, which is also called the transfer function, h, can be derived using the Wiener-Hopf equation, which is that the convolution of the auto-correlation of a system input with the impulse response or transfer function is equal to the cross-correlation of the input and the output or:

$$\Phi_{xy}(t) = \partial h(v)\Phi_{xx}(t-v)dv \tag{4}$$

where:

$$\Phi_{xy}(t) \tag{4a}$$

is the cross-correlation of the input and the output $$\Phi_{xx}(t) \tag{4b}$$

is the auto-correlation of the input and $$h(v) \tag{4c}$$

is the dispersion function, the transfer function or impulse response function.

Equation 4 is a general equation true for any auto-correlation. By proper selection of the auto-correlation function, i.e., if the auto-correlation function is made to be a white noise, the Wiener-Hopf equation is reduced to the simple but important form $$\Phi_{xy}(t) = Kh(t) + B \tag{5}$$

where K is a proportionality constant and B is an offset. This simple form is a consequence of the property that the auto-correlation function has a value only at values of time equal to zero.

The simplified Wiener-Hopf function (Equation 5) may be implemented by means of a pseudo-random noise source having adequate bandwidth for the system for which the impulse response h(t) is sought and which will allow adequate estimation of the cross-correlation function and the auto-correlation function over a finite time. A suitable excitation source is the binary maximum length sequence applied continuously for at least a period of a settling sequence prior to the beginning of the measurement. The binary maximum length sequence is a sequence of binary numbers having the following properties: for n discrete time intervals, the sequence is formed of N discrete time intervals or digits where:

$$N = 2^n - 1 \tag{6}$$

and contains:

$$(N+1)/2 \tag{7}$$

logic one states, and $$(N-1)/2 \tag{8}$$

logic zero states. Further information about the conditions and characteristics of binary maximum length sequences are found in W. D. T. Davies, System Identification for Self-Adaptive Control. ( N.Y.: John Wiley & Sons, 1970.)

Where a binary maximum length sequence is used as an input to a system for cross-correlation purposes to obtain a system impulse response function h(t), the convolution integral from Equation 4 becomes $$\phi_{xy}(t) = a^2 \frac{(N+1)}{N} \Delta t\, h(t) \tag{9}$$

Since in a binary sequence, addition can replace multiplication, the cross-correlation process may be simplified for real-time computation.

Proper identification of the system impulse response function h(t) requires that the period of the sequence length, $T = N\Delta t$, must extend past the time required for the system impulse to decay to essentially zero. Otherwise, folding of the spectrum will occur which yields an incorrect system function.

The same type of restrictions are applicable to the frequency domain.

The computation of the fluid flow, and specifically blood flow, can be derived from Equation 9, noting that the integral over time of the system function h(t) is equal to one by definition. In the discrete form the system function h(t) corresponds to the discrete values $h(k\Delta t)$.

Assuming a unit excitation, the cross-correlation function $\Phi_{xy}$ is scaled by a factor a, where a is equal to the rise in temperature or the increase in indicator at the proximal (inlet) port of the flow system to be measured. Recognizing that:

$$a = P/CF \tag{10}$$

where
P is input power (heat per unit time or rate of indicator infusion per unit time),
C is specific heat of the medium (i.e., blood) or the specific density of the indicator volume in the medium, and
F is flow rate, then it can be shown that flow rate F can be determined by measuring the value of the cross-correlation function of a binary maximum length sequence excitation applied to a system or:

$$F = \frac{(P/C)\frac{N+1}{N}}{\sum_{k=1}^{N} \Phi_{xy}(k\Delta t)} \quad (11)$$

Equation 11 is a very significant expression because it relates flow directly to the cross-correlation function. In this instance the cross-correlation function is the convolution of the impulse response function with a pseudo-random noise auto-correlation function. The chosen input allows for signal processing whereby the signal at the system inlet is cross-correlated with the detected signal at the system outlet. The result can be integrated or more specifically summed, the integration producing upon multiplication of its inverse by a constant a value representative of flow rate, the parameter sought to be measured according to the invention.

In a specific embodiment of the invention, the indicator is heat injected by a heating element capable of modulation between temperature levels; in the alternative the indicator is a dye injected by a driving element capable of on-and-off modulating injections in a fluid injection sequence.

Referring to FIG. 1, there is shown a representative embodiment of measuring apparatus 10 for measuring flow through a fluid system 12, such as a vascular system, between a proximal port 14 and a distal port 16. An indicator quantity q(t), such as heat, is introduced at the proximal port 14 by means of a heating element 18. The change in indicator concentration, such as temperature, is sensed at a transducer 20 at the distal port 16. In one specific embodiment, the heating element 18 may be a fine gauge high-resistance nichrome heating wire mounted on a flow-directed balloon-tipped pulmonary artery catheter, and the transducer 20 may be a thermistor mounted in the same catheter, the catheter being similar in construction to the Swan-Ganz thermodilution catheter.

The heating element 18 is driven by a power source such as an electronic amplifier 22 capable of rapidly switching current between a zero state and a state of continuous power of about 2 to 10 watts in less than about 100 milliseconds. The amplifier 22 is driven by a simulated stochastic signal generator 24. The stochastic signal generator 24 delivers a pseudo-random binary pulse train or random binary length sequence simulating broadband or white noise.

A high gain detector amplifier 26 is coupled to receive signals from the transducer 20. The detector amplifier 26 is capable of detecting microvolt changes in the sensor output, that is, the thermistor output, which changes are indicative of minute changes in the indicator concentration at the distal port 16. The output of the detector amplifier 26 is converted to a digital form by an analog-to-digital converter 28 for convenience of processing.

The signal $X(\Delta t)$ generated by the stochastic generator 24 and a signal $y(\Delta t)$ at the output of the ADC 28 are provided to a cross-correlator 30. The cross-correlator 30 comprises a bank of parallel time delays 31, multipliers 33 and integrators 35 which process in parallel N separate delayed versions of the input binary maximum length sequence by multiplication with the signal y. The output of the cross-correlator 30 is a set of N signals $\Phi_{xy}(k\Delta t)$. The cross-correlator 30 is arranged to allow calculation of all points of the cross-correlation function $\Phi_{xy}(k\Delta t)$ simultaneously. The output of the cross-correlator 30 may thus be considered a parallel sampled signal of a predetermined sequence length T which has been converted from serial time to parallel time. The sequence length T is chosen to be sufficiently long to allow the impulse response function $h(k\Delta t)$ for $k=1 \ldots, N$, to decay essentially to zero.

The output of the cross-correlator 30 is couples to a summer 32. The summer 32 is operative as an integrator to sum all of the points of the cross-correlation functions $\Phi_{xy}$, thereby to obtain a value for the denominator of Equation 11 explained above.

It is normally necessary to obtain a baseline for the dispersion function. To do so, the cross-correlation function is offset to remove bias. Specifically, a response function normalizer 34 is provided which receives as input the output of the cross-correlator 30 over one or more runs and provides as an output the baseline offset factor B as in Equation 5. The response function normalizer 34 operates to compute B based on Equation 5 by assuming first that the response function $h(k\Delta t)$ represents a single decaying exponential process. Then the response function normalizer 34 employs a least means squared error technique for fitting the post peak portion of the impulse response function to the best exponential curve. That impulse response function best fitting the best-fit exponential curve is used to calculate the baseline value B.

The summer 32 provides its output in the form of the sum of parallel cross-correlation functions to a memory 36 wherein data of multiple test runs may be stored. The memory 36 is coupled to a flow rate calculator 38. The flow rate calculator 38 implements the simple algebraic calculations of Equation 11, deriving the cross-correlation function from the memory 36, an offset factor from the response function normalizer 34 and values for power P, specific heat C and sequence length N from external, typically manual, input means 40. The output of the flow rate calculator is connected to a suitable flow rate indicator 39 which indicates or displays the desired value for flow rate through the system comprising the proximal port 14 and the distal port 16, assuming a two port system.

An apparatus according to the invention has been built and tested. A test section representing a vascular system consisted of a mixing chamber and a straight section which mathematically resembled the right heart and pulmonary artery. The volumes were measured directly, and actual flow rate was measured using a Fisher & Porter Type 10A11027A Flowmeter. The fill volumes were measured under nonpulsatile, or constant, flow. Conditions were maintained constant by employing cold water, a constant head tank and a fixed resistance relief valve. A PDP-11 minicomputer was programmed to simulate a cross-correlator. (A commercial cross-correlator, such as apparatus built and sold by Hewlett Packard Company, could have been employed.)

The test apparatus showed that measured flow rate does not deviate significantly from the true flow over a broad range of experimental flow rates. Deviations were attributable to nonideal components, unavoidable noise, quantization error and second order effects due to the assumption that the cross-correlation function $\Phi_{xy}(t)$ is linearly proportional to the impulse response function h(t). The theoretical assumption of equivalence between the cross-correlation function and the system function is justified because the inherent system noise is greater than the magnitude of the higher order components.

Animal studies have also been conducted. A Swan-Ganz flow-directed pulmonary artery catheter was modified to accommodate a heating element as a thermal exciter. Anesthetized dogs received a catheter implant through a femoral vein. A thermistor detector was situated in the pulmonary artery. The heating element exciter was situated in the interior vena cava. Cardiac output was then determined by exciting the heating element with a stochastic input, monitoring the output temperature with reference to time and computing the cross-correlation according to the invention.

Some comments are in order regarding the introduction of error into a practical system designed according to the invention. First, the invention assumes a theoretically perfect input binary maximum length sequence function signal, namely a function signal which assumes only two states exist with infinitely short switching times between the states. In reality, a state transition time is required which might be thought to introduce an error into the auto correlation function. However, if the switching times are short compared to the clock intervals, no significant error is introduced at the excitation. Nevertheless, a non-negligible rise and decay time is present as a result of the time constant of the heating element. However, since a heating element exhibits essentially equal temperature rise and decay times, no corrective measures are required.

Similarly, the output transducer exhibits finite time constants. A thermistor used in a prototype exhibited time constants on the order of 0.1 seconds. However, this time constant was short enough compared to the clock intervals of between 0.5 and 1 seconds that the data was essentially unaffected. As the time constant is lengthened compared to sample times, high frequency information is removed. Since the system impulse response function h(t) is assumed to be a response having relatively few high frequency components, and since high frequency components represent second order effects not a part of the system impulse response, an increase in the output transducer time constants relative to the clock interval serves as an effective and desirable low pass filter function to eliminate undesired high frequency components.

Steady state gain and so-called white noise may be expected to introduce offset error into the system. Since the computation performed by the apparatus according to the invention is equivalent to integrating the system impulse response function to obtain the area or moment, means must be provided to obtain a true baseline for the impulse response function h(t). The use of a curve-fitting exponential technique by means of an element, such as a response function normalizer 34 as herein explained, has been found to be a most effective expedient.

The accuracy of flow measurement by this apparatus is subject to flow variations in the system to be measured, rendering it difficult to obtain an accurate average flow rate. For this purpose, several runs are generally made from which data is obtained. The flow rate calculator may be used to produce an output flow rate for one sample, or it may be employed to average the flow rate over several runs, as desired. This process is roughly equivalent to increasing the integration time or lengthening a single sample run to more accurately determine average flow.

The invention has now been explained with reference to specific embodiments. Other embodiments will be apparent to those of ordinary skill in the art. For example, this invention can be employed wherever direct fluid flow measurement is impractical, as for example, in systems not adapted to the insertion of inline flowmeters excitation. Means other than a variable heat input may be used, such as noninvasive exciters, as indicator dyes and radioactive tracers introduced in the form of a binary maximum length sequence excitation pattern. These indicators could perform equally well, subject to any inherent disadvantages of such indicators. A potential application of the apparatus according to the invention is in multi-port fluid system analysis. A transducer can be provided at each expected outlet port, and the signal output can be cross-correlated in several dimensions to obtain a more accurate reading of average flow at an inlet port. Still further, the present invention can be used for automatic continuous cardiac flow readings, rendering it a potentially important diagnostic tool in the treatment of cardiac conditions. Because of these and other potential modifications, it is not intended that this invention be limited, except as indicated by the appended claims.

I claim:

1. A method for measuring flow of a fluid between a system entry point and a system exit point comprising:
    applying an indicator in the form of a known simulated or actual stochastic excitation signal to said fluid at said system entry point;
    sensing time-dependent response of said fluid to said excitation signal at said system exit point to obtain a response signal;
    cross-correlating said excitation signal with said response signal to construct a cross-correlation function signal;
    extracting a signal representative of said flow rate from said cross-correlation function signal and a knowledge of indicator quantity of said excitation signal; and
    presenting said flow representative signal to a signal utilization means.

2. The method according to claim 1 wherein said extracting step comprises generating said flow representative signal according to the expression $$F = \frac{(P/C)\frac{N+1}{N}}{\sum_{k=1}^{N} \Phi_{xy}(k\Delta t)}$$

where
    F is the flow representative signal,
    P is rate of indicator infusion per unit time,
    C is specific density of indicator volume in said fluid,
    N is the number of intervals in said stochastic excitation signal, Δt is the clock interval, $\Phi_{xy}$ is the cross-correlation function,; and k is an indexing integer.

3. The method according to claim 1 wherein said excitation signal approximates a white noise source.

4. The method according to claim 2 wherein said excitation signal approximates white noise.

5. The method according to claim 1 wherein said excitation signal is a binary maximum length sequence.

6. The method according to claim 2 wherein said excitation signal is a binary maximum length sequence.

7. The method according to claim 1 wherein said applying step comprises applying heat to modulate temperature of said fluid.

8. The method according to claim 1 wherein said applying step comprises introducing an indicator into said fluid to modulate indicator concentration in said fluid.

9. The method according to claim 8 wherein said indicator is a dye.

10. The method according to claim 8 wherein said indicator is a radioactive isotope.

11. The method according to claim 1 further including the step of establishing a baseline for said cross-correlating step.

12. The method according to claim 11 wherein said establishing step comprises approximating said cross-correlation function signal as an exponential decaying function and selecting as a baseline a value corresponding to an asymptote of said exponential decaying function.

13. The method according to claim 12 wherein said approximating step comprises least-means-squared curve fitting of said cross-correlation function signal to selected exponential decaying functions to determine a best fit exponential decaying function.

14. An apparatus for measuring flow comprising:
means for providing an indicator in the form of a known simulated or actual stochastic excitation signal at an inlet port of a system whose flow rate is to be measured;
means for detecting changes in a fluid parameter of said system in response to said excitation signal at said inlet port of said system, said detecting means disposed at an outlet port of said system and operative to generate a detected signal;
means for cross-correlating said excitation signal and said detected signal to obtain a cross-correlation function signal, said cross-correlation function signal being substantially linearly related to a characteristic impulse response of said system;
means for integrating signals representative of a plurality of said cross-correlation function signals to produce a sum of cross-correlation function signals; and
means responsive to said sum of cross-correlation function signals for generating a system output signal representative of the measured flow rate.

15. The apparatus according to claim 14 wherein said signal providing means is operative to generate a pseudo-random signal approximating a white noise source.

16. The apparatus according to claim 14 wherein said signal providing means is operative to generate said excitation signal in the form of a binary maximum length sequence.

17. The apparatus according to claim 14 wherein said signal providing means comprises means for injecting an indicator in modulated quantity at said system inlet point, and wherein said detecting means includes means for detecting concentration of said indicator.

18. The apparatus according to claim 14 wherein said signal providing means comprises means for applying heat in modulated quantity at said inlet point, and wherein said detecting means includes means for detecting temperature of said fluid indicative of temperature changes induced by said applied heat.

19. The apparatus according to claim 14 further including means for calibrating said system output signal by establishing a baseline for said cross-correlation function signals.

20. The apparatus according to claim 19 wherein said calibrating means includes means for approximating said cross-correlation function signal as an exponential decaying function and means for selecting as a baseline a value corresponding to an asymptote of said exponential decaying function.

* * * * *